United States Patent [19]

Desmurs et al.

[11] Patent Number: 5,334,735
[45] Date of Patent: Aug. 2, 1994

[54] PROCESS FOR PREPARING CHLORANIL

[75] Inventors: Jean-Roger Desmurs, Communay; Isabelle Jouve, Villeurbanne, both of France

[73] Assignee: Rhone-Poulenc Chimie, Courbevoie, France

[21] Appl. No.: 26,079

[22] Filed: Mar. 4, 1993

Related U.S. Application Data

[63] Continuation of Ser. No. 622,113, Dec. 6, 1990, abandoned, which is a continuation of Ser. No. 301,892, Jan. 26, 1989, abandoned.

[30] Foreign Application Priority Data

Jan. 27, 1988 [FR] France ................. 88 00910

[51] Int. Cl.⁵ ........................ C07C 50/24; C07C 46/06
[52] U.S. Cl. ........................ 552/308; 568/765
[58] Field of Search ................ 552/308; 568/765

[56] References Cited

U.S. PATENT DOCUMENTS 2,722,537 11/1955 Fox .................... 260/396 R

FOREIGN PATENT DOCUMENTS 220135 4/1987 European Pat. Off. .
2645114 4/1978 Fed. Rep. of Germany .

OTHER PUBLICATIONS

R. Schuloff and R. Pollak, Chemiker-Zeitung, No. 58, pp. 569–570 (1932).
Fischer and Henderson, Synthesis, Jun./Jul. 1985, pp. 641–643.
Rettig and Latscha, Z. Naturforsch, 35 b, pp. 399–400 (1980).

*Primary Examiner*—Arthur C. Prescott
*Attorney, Agent, or Firm*—Finnegan, Henderson, Farabow, Garrett & Dunner

[57] ABSTRACT

Process for preparing chloranil by the oxidative chlorination of a quinone or of a hydroquinone with a hydrochloric acid/hydrogen peroxide mixture, the introduction of hydrogen peroxide being carried out at a temperature above 60° C.

15 Claims, No Drawings

PROCESS FOR PREPARING CHLORANIL

This application is a continuation of application Ser. No. 07/622,113, filed Dec. 6, 1990, now abandoned, which is a continuation of application Ser. No. 07/301,892, filed Jan. 26, 1989, now abandoned.

The present invention relates to a new process for preparing chloranil from a hydroquinone or from a quinone, the hydroquinone being optionally chlorinated and the quinone being optionally partially chlorinated. The present invention is capable of being carried out in the simplest possible installation.

Chloranil is the common name for tetrachlorobenzoquinone and is a well-known intermediate used in the synthesis of dyestuffs. Many processes for the synthesis of chloranil are described in the literature; the yields disclosed for some of these processes are of such excellence as 95% and above.

For example, the chlorination of quinone in the presence of concentrated solutions of hydrochloric acid is described by R. Schuloff and R. Pollak in Chemiker-Zeitung 56, pp. 569–570 (1932). The chlorination is performed at high temperatures during very long reaction periods. Due to the high temperatures and the large amounts of chlorine which are used, a portion of the chloranil sublimates, which must be condensed to be recovered. In addition, the unreacted excess chlorine creates pollution problems.

Many chlorination processes are known which utilize concentrated hydrochloric acid ill the presence of miscellaneous catalysts. For example, a process for the oxidative chlorination of hydroquinone in tile presence of magnesium dichloride and hydrogen peroxide is described in German Patent 2,645,114 ( See Comparative Example 1 herein). In Fischer and Henderson, Synthesis, June–July 1985, pp. 641-3, the oxidation of hydroquinones, catechols and phenols is performed in the presence of ceric ammonium nitrate or ammonium dichromate. In Rettig and Latscha, Z. Naturforsch, 35 b, pp. 399–400 (1980), the chlorination is performed in the presence of antimony pentachloride. The industry has long sought to avoid the use of such chlorination catalysts in processes for making chloranil.

Thus, a process for the oxidative chlorination of hydroquinone or of quinone in the absence of any catalyst has been proposed in European Patent 220,135, the process being characterized by the use of a high chlorine pressure of between 3 and 40 bar. The hydroquinone concentration in the hydrochloric acid never exceeds 70 g/liter, which is low for an industrial process and, in addition, the high pressure requires the use of special equipment.

The preparation of chloranil from phenolic sources has been abandoned by the chemical industry, since byproducts of the dioxin type are formed during tile oxidative chlorination. Dioxins are so toxic that their presence must be avoided at all costs (German decree on dangerous substances of September 1986 §9(6)).

The present invention can solve the problems of the prior art, i.e., it can enable the reaction to take place in the absence of halometallic catalysts, allow the reaction to be conducted at atmospheric pressure, and lastly enable the use of high concentrations of starting materials, of the order of 100 g per liter of reaction mixture.

The present invention provides a process for preparing chloranil comprising contacting a quinone, which may be unsubstituted or partially chlorinated or a hydroquinone, which may be unsubstituted or chlorinated, with a hydrochloric acid/hydrogen peroxide mixture, in the substantial absence of a chlorination catalyst for a time sufficient to form the chloranil, wherein the hydrogen peroxide is introduced at a temperature above 60° C., preferably above 70° C.

German Patent No. 2,645,114, referred to earlier, discloses introducing cold hydrogen peroxide at the beginning of the reaction. This causes an accumulation of hydrogen peroxide in the reactor, which creates safety problems and can lead to considerable foam formation and resulting difficulties in controlling the reaction.

The introduction of hydrogen peroxide into the heated reaction medium in the process of the present invention is preferably carried out in continuous fashion to avoid the accumulation of the peroxide in the reactor.

The optionally partially chlorinated quinone may preferably be represented by formula (I)

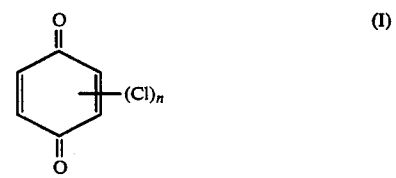

in which n is equal to or greater than 0 and equal to or less than 3.

The optionally chlorinated hydroquinone may preferably be represented by formula (II)

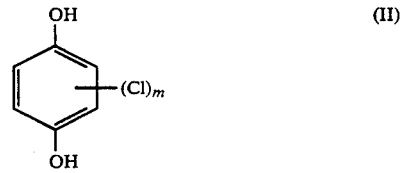

in which m is equal to or greater than 0 and equal to or less than 4.

It is preferable to use unsubstituted hydroquinone as a starting material, since it represents the least expensive starting material.

It is advantageous to use a reaction medium saturated with hydrochloric acid. For this purpose, it is preferable to use an aqueous hydrochloric acid solution which is 10 N, or containing 30 to 37% by weight of hydrochloric acid. To saturate the medium, it is advantageous to introduce gaseous hydrochloric acid in continuous fashion.

The hydrogen peroxide solution should be as concentrated an aqueous solution as possible. A solution containing approximately 30% by weight of hydrogen peroxide is preferred.

At least 5 moles of hydrogen peroxide per mole of the hydroquinone are preferably used, and a 20% hydrogen peroxide excess over the 5:1 ratio is more preferably employed. When the quinone is used as starting material, at least 4 moles of hydrogen peroxide per mole of quinone are preferably used, and a 20% hydrogen peroxide excess over the 4:1 ratio is more preferably employed.

The quinone or hydroquinone is introduced into the reaction medium consisting of hydrochloric acid at a concentration preferably less than 130–140 g/liter. A concentration of approximately 100 g/liter is more preferred.

The process of the invention is carried out at a reaction temperature above 60° C., preferably above 70° C., and more preferably at 80°–90° C. A temperature of approximately 90° C. is most advantageous.

The reaction pressure is preferably atmospheric pressure.

The following examples will enable a better understanding of the invention to be gained. They are exemplary only and must not be considered to limit the invention.

The following abbreviations will be used:
—HQ: hydroquinone
—Cl$_3$BQ: trichlorobenzoquinone
—Cl$_4$HQ: tetrachlorohydroquinone
—RY: yield relative to the product

COMPARATIVE EXAMPLE 1

A comparative experiment was conducted according to the process disclosed by German Patent No 2,645,114 referred to above. A 500-ml reactor equipped with a central paddle stirrer, a condenser, a dropping funnel and a thermometer was charged with 200 ml of 35% strength hydrochloric acid (2.28 tool), 17.63 g of MgCl$_2$.6H$_2$O (0.086 mol) and 2.82 g of hydroquinone (0.0256 mol).

After the reaction mixture had been brought to 0° C., 15 ml of 30% strength hydrogen peroxide (0.146 mol) were introduced over a period of 15 minutes. The mixture was then brought to 100° C. in the course of 1 hour 30 minutes, which caused the formation of foam rising in the condenser. After 'two hours' heating at 100° C., the mixture was cooled and the precipitate was then collected by filtration on a sintered filter. The precipitate was washed with 3×20 ml of water and dried in the oven. The precipitate collected weighed 5.89 g, equivalent to 93.6% by weight of the expected chloranil. Liquid phase chromatographic assay of this product showed that it contained 49.2% of chloranil and 44.8% of tetrachlorohydroquinone, leading to RY values of 46.2% and 41.7%, respectively. The crude product also contained 6% of magnesium chloride.

EXAMPLES 1 AND 2

Two examples were carried out according to the invention. These examples were basically conducted as in Comparative Example 1. Differences include the fact that the hydrogen peroxide was introduced into a hydrochloric acid solution containing the hydroquinone maintained at 80° C. in the absence of a catalyst (MgCl$_2$). Note also that in Comparative Example 1, the hydrogen peroxide was introduced over a period of 15 minutes, whereas in Example 1, the hydrogen peroxide was introduced over 50 minutes and in Example 2, the hydrogen peroxide was introduced over 20 minutes.

Moreover, the initial hydroquinone concentration differed in the three experiments. The reaction conditions and results of these examples are illustrated in Table 1. Note that the heating times and temperatures also differed in the experiments.

It can be seen from the results in Table 1 that Examples 1 and 2, conducted according to the present invention, not only eliminated the presence of foam which resulted from the process of Comparative Example 1, but also realized much greater purity of chloranil in the reaction product.

| Experiment | Initial HQ concentration | Excess H$_2$O$_2$ | Addition H$_2$O$_2$ Time | Addition H$_2$O$_2$ Temperature | Heating Time | Heating Temperature | Yld product isolated | Composition Chloranil | Composition Cl$_3$BQ | Composition Cl$_4$HQ |
|---|---|---|---|---|---|---|---|---|---|---|
| Comparative | 14 g/l | 20% | 15' | 0° C. | 1 H 30 2 H | 0 to 100° C. 100° C. | 93.9% | 49.2% | | 44.8% |
| 1 | 15 g/l | 20% | 50' | 80° C. | 60' | 90° C. | 92.8% | 89.4% | 5.3% | 5% |
| 2 | 18 g/l | 20% | 20' | 80° C. | Filtration in the heated state at 80° C. | | 82% | 97.8% | 0.8% | |

Comparative: substantial foam
Experiments 1 and 2: absence of foam

We claim:

1. A process for preparing chloranil comprising contacting a quinone or hydroquinone with hydrochloric acid to form a mixture, heating the mixture to a temperature above 60° C., and contacting said mixture at a temperature above 60° C. with hydrogen peroxide for a time sufficient to form the chloranil, wherein the reaction takes place in the substantial absence of a chlorination catalyst.

2. The process as claimed in claim 1, wherein said quinone is partially chlorinated.

3. The process as claimed in claim 1, wherein said hydroquinone is chlorinated.

4. The process as claimed in claim 1, wherein said mixture is heated to a temperature above 70° C. prior to contact with said hydrogen peroxide.

5. The process as claimed in claim 1, wherein the quinone is represented by formula (I)

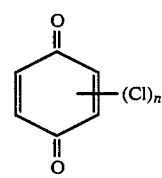

(I)

in which n is equal to or greater than 0 and equal to or less than 3.

6. The process as claimed in claim 1, wherein the hydroquinone is represented by formula (II)

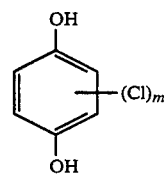

(II)

in which m is equal to or greater than 0 and equal to or less than 4.

7. The process as claimed in claim 6, wherein m is equal to 0.

8. The process as claimed in claim 1, wherein the hydrochloric acid is an aqueous solution containing from 30 to 37% hydrochloric acid.

9. The process as claimed in claim 1, wherein the hydrogen peroxide is an aqueous solution containing approximately 30% by weight of hydrogen peroxide.

10. The process as claimed in claim 1, wherein the reaction temperature ranges from 80° to 90° C.

11. The process as claimed in claim 1, wherein the reaction pressure is atmospheric pressure.

12. The process as claimed in claim 1, wherein the concentration of quinone or hydroquinone is less than 130-140 g/liter of hydroquinone and hydrochloric acid or quinone and hydrochloric acid.

13. The process as claimed in claim 12, wherein said concentration of hydroquinone or quinone is approximately 100 g/liter, 14. The process as claimed in claim 1, wherein the concentration of hydrogen peroxide is at least 5 moles per mole of hydroquinone.

15. The process as claimed in claim 1, wherein the concentration of hydrogen peroxide is at least 4 moles per mole of quinone.

* * * * *